(12) United States Patent
Wagner et al.

(10) Patent No.: US 6,737,546 B2
(45) Date of Patent: May 18, 2004

(54) EXTRACTION PROCESS FOR RECOVERY OF ACRYLIC ACID

(75) Inventors: David R. Wagner, Naperville, IL (US); Steve J. Miko, Hudson, OH (US)

(73) Assignee: Lurgi AG, Frankfurt (DE)

( * ) Notice: Subject to any disclaimer, the term of this patent is extended or adjusted under 35 U.S.C. 154(b) by 167 days.

(21) Appl. No.: 10/008,641

(22) Filed: Nov. 13, 2001

(65) Prior Publication Data

US 2003/0092937 A1 May 15, 2003

(51) Int. Cl.[7] .............................................. C07C 51/42
(52) U.S. Cl. ...................... 562/600; 562/545
(58) Field of Search ................. 562/600, 545

(56) References Cited

U.S. PATENT DOCUMENTS

| | | | |
|---|---|---|---|
| 3,689,541 A | 9/1972 | Sennewald et al. | 260/526 |
| 3,781,192 A | 12/1973 | Wood et al. | 195/100 |
| 3,939,096 A | 2/1976 | Richardson | 252/456 |
| 3,962,074 A | 6/1976 | Schropp | 210/21 |
| 3,962,322 A | 6/1976 | Richardson | 260/530 |
| 3,968,153 A | 7/1976 | Ohrui et al. | 260/526 |
| 4,092,354 A | 5/1978 | Shiraishi et al. | 260/530 |
| 4,092,355 A | 5/1978 | Leonard et al. | 260/530 |
| 4,097,523 A | 6/1978 | Kao et al. | 260/530 |
| 4,115,440 A | 9/1978 | Sheng et al. | 562/533 |
| 4,124,633 A | 11/1978 | Leonard et al. | 562/598 |
| 4,144,399 A | 3/1979 | Sheng et al. | 562/598 |
| 4,203,906 A | 5/1980 | Takada et al. | 260/346.4 |
| 4,537,874 A | 8/1985 | Sato et al. | 502/311 |
| 5,315,037 A | 5/1994 | Sakamoto et al. | 562/545 |
| 5,910,607 A | 6/1999 | Sakakura et al. | 562/532 |

FOREIGN PATENT DOCUMENTS

| EP | 0 861 820 | 9/1998 | ........... C07C/51/46 |
|---|---|---|---|
| EP | 0861820 A3 | * 10/1998 | |

* cited by examiner

*Primary Examiner*—Paul J. Killos
*Assistant Examiner*—Hector M. Reyes
(74) *Attorney, Agent, or Firm*—Norris McLaughlin & Marcus (57) ABSTRACT

Economical processes are disclosed for recovery and refining of at least acrylic acid from a gaseous mixture such as is obtainable by gas-phase catalytic oxidation of propylene. Processes of the invention include quenching the gaseous mixture with an aqueous quench liquid to obtain an aqueous solution comprising the acid values; contacting the aqueous solution with an immiscible extraction solvent; and an integrated sequence of distillations and phase separations to recover for recycle organic components of the extraction solvent, and obtain valuable acrylic acid and acetic acid products. Advantageously, the immiscible extraction solvent is substantially free of aromatic compounds such as benzene and toluene.

20 Claims, 1 Drawing Sheet

EXTRACTION PROCESS FOR RECOVERY OF ACRYLIC ACID

FIELD OF THE INVENTION

The field of this invention relates to continuous processes for recovery of acid values from hot gaseous mixtures which are obtained by catalytic oxidation of hydrocarbon compounds with a dioxygen containing gas. More particularly, this invention relates to recovery and refining acid values of at least acrylic acid from a gaseous mixture such as is obtainable by gas-phase catalytic oxidation of propylene. Processes of the invention include quenching the gaseous mixture with an aqueous quench liquid to obtain an aqueous solution comprising the acid values; contacting the aqueous solution with an immiscible extraction solvent; and an integrated sequence of distillations and phase separations to recover for recycle organic components of the extraction solvent, and obtain valuable acrylic acid and acetic acid products. Advantageously, according to the invention the immiscible extraction solvent is substantially free of aromatic compounds such as benzene and toluene.

BACKGROUND OF THE INVENTION

As is well known, most of the commercial acrylic acid is produced from propylene by heterogeneous catalytic oxidation of propylene and/or acrolein in the vapor phase with air and steam. Generally, the two methods for the vapor phase oxidation of propylene are one-stage and two-stage processes. Typically, the process is carried out in two stages giving first acrolein and then acrylic acid. Higher selectivity is possible by using different catalyst compositions and reaction conditions for each of the two stages.

Acrylic acid and esters thereof undergo reactions characteristic of both unsaturated organic compounds and aliphatic carboxylic acids or esters. Acrylic acid and its esters polymerize very easily. Acrylates and acrylic acid are primarily used to prepare emulsion and solution polymers. Emulsion polymerization processes provide high yields of polymers in a form suitable for a variety of applications. Acrylate polymer emulsions are useful as coatings, finishes, and binders for leather, textiles, and paper. Acrylate emulsions are used in the preparation of both interior and exterior paints, floor polishes, and adhesives. Solution polymers of acrylates, frequently with minor concentrations of other monomers, are employed in the preparation of industrial coatings. Polymers of acrylic acid can be used as super-absorbents in disposable diapers, as well as in formulation of superior, reduced-phosphate-level detergents.

Polymerization of acrylic acid and its esters is catalyzed by heat, light, and peroxides and inhibited by compounds such as the monomethyl ether of hydroquinone or hydroquinone, provided oxygen in present. The spontaneous polymerization of acrylic acid is extremely violent.

Commercial production of organic acids is typically accomplished by catalytic oxidation of hydrocarbon compounds having at least one double bond with an oxygen. In particular, production of acrylic acid through gas-phase catalytic oxidation of propylene and/or acrolein is a widely practiced industrial process. This process normally consists of an oxidation step to catalytically oxidize propylene and/or acrolein using molecular oxygen in gaseous phase, a collection step of contacting an aqueous liquid with an acrylic acid-containing gas resulting from the gas-phase catalytic oxidation, and a recovery step to isolate and refine acrylic acid from the aqueous solution of the acrylic acid which is obtained in the collection step.

Unavoidably the acrylic acid-containing gas also contains such co-products as acetaldehyde, formaldehyde, formic acid, and acetic acid, among which acetic acid is in relatively large quantity. For producing high purity acrylic acid, therefore, acetic acid must be removed. Attempts to remove the acetic acid in the acrylic acid by means of distillation, however, tend to induce polymerization of acrylic acid because of the required high distillation temperature. (Boiling point of acetic acid is about 118° C.) There is also another problem that the small specific volatility values of acrylic acid and acetic acid render their separation by simple distillation difficult.

Consequently, with the view to isolate and recover high purity acrylic acid from said aqueous acrylic acid solution, that is, to separate acrylic acid from acetic acid and water to recover high purity acrylic acid which is substantially free from acetic acid and water, normally a method of distilling the aqueous acrylic acid solution in an azeotropic separation column in the presence of an azeotropic solvent is adopted.

A process for isolating acrylic acid from aqueous crude acrylic acid by extraction with a ketone and a complex system of distillations is described in U.S. Pat. No. 3,689,541 in the name of Kurt Sennewald, Heinz Erpenbach, Heinz Handte and Winfried Lork. In this process a liquid—liquid extraction of the aqueous stream uses 3,3,5-trimethylcyclohexanone and/or isophorone as the extractant(s). The extract, containing acrylic acid, acetic acid, high boilers and minor proportions of water which are dissolved in the extractant, is introduced into a first distilling column, which is operated under reduced pressure; the bottom product of the first distilling column, containing the high boilers and the extractant(s) is recycled to the extraction; distillate containing acrylic acid, acetic acid, water and minor proportions of extractant(s) is fed to a second distilling column, which is operated under reduced pressure; a mixture of water and extractant(s) is distilled off; the bottom product of the second distilling column, containing acrylic acid and acetic acid is fed to a third distilling column, which is operated under reduced pressure; and acetic acid is separated as a distillate and acrylic acid is recovered as a bottom product.

Later, U.S. Pat. No. 3,781,192 in the name of Kurt Sennewald, Heinz Erpenbach, Heinz Handte, Georg Kohl and Winfried Lork, describes an extractive azeotropic distillation of aqueous crude acrylic acid using 3,3,5-trimethylcyclohexanone as the distillation aid under a pressure between 20 an 80 mm mercury. The bottom product is said to contain acrylic acid, acetic acid and minor proportions of 3,3,5-trimethylcyclohexanone, residual formaldehyde and higher boiling constituents. Acrylic acid contaminated with 3,3,5-trimethylcyclohexanone is recovered as a distillate, which is separated by further distillations.

Several other organic mixtures have been said to be useful to extract acrylic acid from aqueous solution. For example, U.S. Pat. No. 3,962,074 in the name of Wilhelm Karl Schropp describes acrylic acid separation from aqueous solution by extraction of the solution with a mixture of from 1 to 50 parts by weight of butanol and from 1 to 10 parts by weight of butyl acrylate. U.S. Pat. No. 3,968,153 in the name of Tetsuya Ohrui, Yasuhito Sakakibara, Yukinaga Aono, Michio Kato, Hiroshi Takao and Masami Ayano describes extraction of acrylic acid from aqueous solution with methylethylketone containing from 5 to 20 percent by weight of a xylene or ethylbenzene.

U.S. Pat. No. 5,315,037 in the name of Kazuhiko Sakamoto, Hiroaki Tanaka, Masatoshi Ueoka, Yoji Akazawa and Masao Baba assigned to Nippon Shokubai Co., Osaka, Japan states that a process for producing acrylic acid wherein a mixed gas of acrylic acid and by-products produced by catalytic gas phase oxidation of propylene and/or acrolein is contacted with water to obtain an aqueous solution for azeotropic distillation may be improved by using a mixed solvent consisting of A at least one member selected from the group consisting of diethyl ketone, methyl propyl ketone, methyl isobutyl ketone, methyl-tert-butyl ketone and n-propyl acetate and B at least one member selected from the group consisting of toluene, heptane and methylcyclohexane. According to this process the mixing ratio between A and B must be the range of 50:50 to 75:25 of the weight basis. If the amount of A exceeds the above range, the concentration of acetic acid at the bottom of the azeotropic distillation tower is said to become too high. On the contrary, when B is used in larger amounts than the above range, the amount of acrylic acid distilled from the tower top is increased which increase is undesirable.

More recently U.S. Pat. No. 5,910,607 in the name of Yasuyuki Sakakura, Masahiko Yamagishi and Hirochika Hosaka assigned to Mitsubishi Chemical Corp., Tokyo, Japan, states that a process for producing acrylic acid, wherein propylene and/or acrolein is catalytically oxidized with molecular oxygen in a vapor phase and the gas resulting from the oxidation is cooled and/or absorbed in water to form a crude aqueous acrylic acid, followed by azeotropic distillation to remove the water with an entrainer of a boiling point of 80° to 130° C. on the crude aqueous acrylic acid which may have, upon necessity, undergone removal of aldehydes contained therein to produce acrylic acid purified in that the crude aqueous acrylic acid is substantially dehydrated may be improved by conducting the azeotropic distillation under such conditions that concentrations of the entrainer and water in the bottom product of the azeotropic distillation are, respectively, from 5 percent to 30 percent by weight (entrainer) and no higher than 0.05 percent by weight (water). Where the entrainer is required to azeotropically boil with water, the entrainer is selected from the group consisting of alkyl ester of acetic acid and methyl-isobutyl ketone. Where the entrainer is required to azeotropically boil with both water and acetic acid, the entrainer is selected from the group consisting of aliphatic and aromatic hydrocarbons and isobutyl ether. Preferably concentrations of the entrainer and water in the bottom product of the azeotropic distillation are, respectively, from 6 percent to 15 percent by weight, more preferably 6 to 13 percent (entrainer) and 0.3 percent to 0.05 percent (water).

It is therefore a general object of the present invention to provide an improved process which overcomes the aforesaid problem of prior art methods for production of acid values which include at least acrylic acid.

More particularly, it is an object of the present invention to provide an improved method for recovery of acid values from an aqueous solution using an immiscible extraction solvent within an integrated sequence of distillations and phase separations to recover for recycle organic components of the extraction solvent, and obtain valuable acrylic acid and acetic acid products.

Advantageously, the improved processes of the invention should use only immiscible extraction solvents which are substantially free of aromatic compounds such as benzene.

Other objects and advantages of the invention will become apparent upon reading the following detailed description and appended claims.

SUMMARY OF THE INVENTION

Economical processes are disclosed for recovery of acid values from a gaseous mixture formed by catalytic oxidation of propylene in the vapor phase with a dioxygen containing gas and steam. Acid values of acrylic acid and acetic acid produced in the catalytic oxidation reactors is recovered from product gaseous stream as a aqueous solution. Solvent extraction is used to separate most of the water from the aqueous acid solution. Components of the immiscible extraction solvent and low boiling impurities are separated from the acid values by distillation.

Processes of this invention comprise: (a) quenching the gaseous mixture comprising acid values of acrylic acid and acetic acid, steam and one or more non-condensable gas with an aqueous quench liquid to form an aqueous solution comprising acid values; (b) contacting the aqueous solution with an immiscible solvent comprising propyl acetate and a cyclohexane to form an organic extract comprising acid values and a major portion of the propyl acetate, and an aqueous raffinate comprising a minor portion of the propyl acetate; (c) fractionating the organic extract as by distillation to obtain a high boiling fraction substantially free of cyclohexane, preferably less than 1 percent by weight of cyclohexane, and a low boiling fraction comprising cyclohexane and steam; and thereafter (d) fractionating the high boiling fraction to obtain an acrylic acid product substantially free of propyl acetate and a propyl acetate fraction comprising propyl acetate and acetic acid.

Typically, the aqueous solution formed by quenching a gaseous mixture produced by catalytic oxidation of propylene contains up to about 80 percent acrylic acid, preferably from about 25 to about 75 percent of acrylic acid, more preferably from about 30 to about 70 percent of acrylic acid, and most preferably from about 40 to about 60 percent of acrylic acid for best results. Generally, the aqueous solution can also contain up to about 10 percent acetic acid, preferably from about 0.5 to about 7.5 percent of acetic acid, more preferably from about 1.0 to about 5.0 percent of acetic acid, and most preferably at least about 1.5 percent of acetic acid.

In a preferred embodiment of the invention, the aqueous solution comprises from about 30 to about 70 percent of acrylic acid, from about 0.5 to about 7.5 percent of acetic acid and from about 15 to about 65 percent of water based upon the weight of the aqueous solution.

Advantageously, according to the invention the immiscible solvent comprises at least isopropyl acetate and a substantial amount of cyclohexane, in particular no less than about 25 percent of cyclohexane based upon the total weight of isopropyl acetate and a substantial amount cyclohexane. Preferably, according to the invention the immiscible solvent comprises isopropyl acetate and from about 30 to about 80 percent of cyclohexane based upon the total weight of isopropyl acetate and cyclohexane, more preferably about 35 to about 75 percent, most preferred about 45 to about 65 for best results.

Contacting of the aqueous solution with immiscible solvent may employ any of the many known methods for liquid-liquid extraction. In a preferred embodiment of the invention the contacting is carried out using a continuous extraction system with counter-current flow of the aqueous solution and the immiscible solvent. Likewise in preferred embodiments of the invention the integrated sequence of distillations and phase separations are carried out using continuous systems to separate the desired product or products and recover for recycle organic components of the extraction solvent.

An aspect of special significance is condensing at least a portion of the low boiling fraction thereby forming condensate comprising immiscible aqueous and cyclohexane phases, and separating a recovered cyclohexane stream from the aqueous phase. The recovered cyclohexane is advantageously recycled as a component of the immiscible solvent.

In a preferred embodiment of the invention, the acrylic acid product contains less than 0.1 percent by weight of acetic acid. In another embodiments of the invention, the acrylic acid product more preferably contains less than 0.07 percent by weight of acetic acid and most preferably less than 0.05 percent by weight of acetic acid. In yet another preferred embodiment of the invention, the propyl acetate fraction comprises from about 80 to about 93 percent of propyl acetate and from about 2 to about 15 percent of acetic acid based upon the weight of the propyl acetate fraction.

In preferred embodiments of the invention, at least 90 percent of the acrylic acid contained in the aqueous solution is recovered in the acrylic acid product.

One aspect of the invention provides a process for recovery of acid values from a gaseous mixture formed by catalytic oxidation of propylene with a gaseous source of dioxygen which process comprises: (a) quenching the gaseous mixture comprising acid values of acrylic acid and acetic acid, steam and one or more non-condensable gas with an aqueous quench liquid to form an aqueous solution comprising acid values; (b) contacting the aqueous solution with an immiscible solvent comprising propyl acetate and a cyclohexane to form an organic extract comprising acid values and a major portion of the propyl acetate, and an aqueous raffinate comprising a minor portion of the propyl acetate; (c) fractionating the organic extract as by distillation to obtain a high boiling fraction substantially free of cyclohexane and a low boiling fraction comprising cyclohexane and steam; (d) fractionating the high boiling fraction to obtain an acrylic acid product substantially free of propyl acetate and a propyl acetate fraction comprising propyl acetate and acetic acid; and (e) fractionating the propyl acetate fraction to obtain an acetic acid product substantially free of propyl acetate and a recovered propyl acetate fraction. Advantageously the immiscible solvent contains at least a portion of the recovered propyl acetate fraction.

Processes of the invention preferably include condensing at least a portion of the low boiling fraction thereby forming condensate comprising immiscible aqueous and cyclohexane phases, and separating a recovered cyclohexane phase from the aqueous phase. Recovered cyclohexane is advantageously recycled as a component of the immiscible solvent system.

Other embodiments of the invention preferably include forming a stripping tower feed by combining at least a portion of the separated aqueous phase with at least a portion of the aqueous raffinate, and contacting the stripping tower feed with steam to recover solvents and beneficially obtain wastewater suitable for bio-treatment.

Another aspect of the invention provides a process for recovery of acid values from a gaseous mixture formed by catalytic oxidation of propylene with a gaseous source of dioxygen which process comprises: (a) quenching the gaseous mixture comprising acid values of acrylic acid and acetic acid, steam and one or more non-condensable gas with an aqueous quench liquid to form an aqueous solution comprising acid values; (b) contacting at least a portion of the aqueous solution with an immiscible solvent comprising propyl acetate and a cyclohexane to form an organic extract comprising acid values and a major portion of the propyl acetate, and an aqueous raffinate comprising a minor portion of the propyl acetate; (c) fractionating at least a portion of the organic extract as by distillation to obtain a high boiling fraction substantially free of cyclohexane and a low boiling fraction comprising cyclohexane and steam; (d) condensing at least a portion of the low boiling fraction to form a mixture of at least two immiscible liquid phases, and separating from the mixture a recovered cyclohexane phase containing less than about 2 percent by weight of water, preferably less than about 1 percent, more preferably less than 0.5 percent by weight; (e) fractionating the high boiling fraction to obtain an acrylic acid product substantially free of propyl acetate and a propyl acetate fraction comprising propyl acetate and acetic acid; and (f) fractionating the propyl acetate fraction to obtain an acetic acid product substantially free of propyl acetate and a recovered propyl acetate fraction. The immiscible solvent beneficially contains at least a portion of the recovered cyclohexane phase. Advantageously the immiscible solvent contains at least a portion of the recovered propyl acetate fraction and at least a portion of the recovered cyclohexane phase.

Another aspect of special significance is the process wherein the fractionating of the organic extract is carried out in a continuous distillation system using as reflux at least a portion of the recovered cyclohexane.

In preferred embodiments of the invention, the immiscible solvent, comprising propyl acetate and a cyclohexane, contains less than a total of about 10 percent by weight of acrylic acid and acetic acid. More preferably the immiscible solvent contains less than a total of about 5 percent by weight of acrylic acid and acetic acid, and most preferably less than about 2 percent.

For a more complete understanding of the present invention, reference should now be made to the embodiments illustrated in greater detail in the accompanying drawing and described below by way of examples of the invention.

BRIEF DESCRIPTION OF THE FIGURE

The appended claims set forth those novel features which characterize the present invention. The present invention itself, as well as advantages thereof, may best be understood, however, by reference to the following brief description of preferred embodiments taken in conjunction with the annexed drawing, in which:

BRIEF DESCRIPTION OF THE INVENTION

Figure 1:
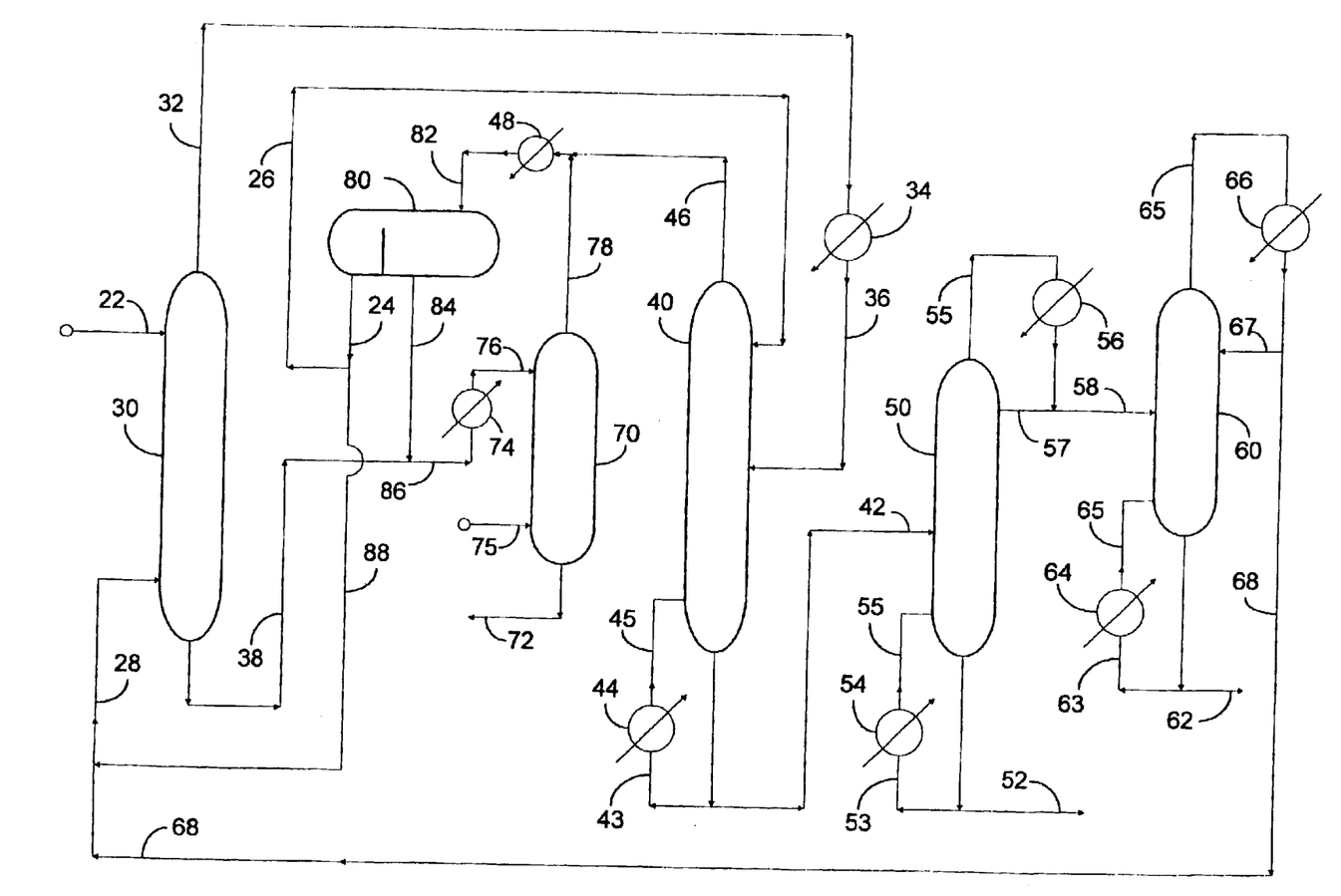
The FIGURE is a schematic diagram of a preferred method for operating the process of this invention in the continuous mode being arranged to provide an integrated sequence of extractions, distillations and phase separations to recover for recycle organic components of the extraction solvent and to maintain suitable operating conditions in accordance with the present invention, and thereby obtain valuable acrylic acid and acetic acid products.

Processes of this invention are particularly suitable for use in recovery and refining acid values of acrylic acid and, optionally, acetic acid from a gaseous mixture produced, generally, by gas-phase catalytic oxidation and/or thermal oxidation of propylene, acrolein, or propane.

While single-stage oxidation processes are known, higher selectivity is possible by optimizing catalyst composition and reaction conditions for each of two stages. Because of the more efficient utilization of raw material and catalysts, all known commercial facilities use two separate stages of oxidation, typically a two-stage continuous process without isolation of the intermediate acrolein. A mixture of propylene, air, and steam is converted to acrolein in the first reactor. The effluent from the first reactor is then transferred directly to the second reactor where the acrolein is oxidized primarily to acrylic acid in about 80 to about 95 percent yield based on propylene. The products are collected water to give up to about 80 percent aqueous acrylic acid, preferably from about 25 to about 75 percent of acrylic acid, more preferably from about 30 to about 70 percent of acrylic acid, and most preferably from about 40 to about 60 percent of acrylic acid for best results.

As is well known, performance of the oxidation catalysts is an important factor, perhaps the most significant factor, in the economics of this and other oxidation processes. Catalyst performance is measured by activity, i.e., conversion of reactants, selectivity, i.e. conversion of reactant to desired product, rate of production of desired product per unit of reactor volume per unit of time, and catalyst life, i.e. effective time on-stream before significant loss of activity or selectivity.

Preferably processes of this invention derive a suitable gaseous mixture from a two stage catalytic oxidation of propylene with a gaseous source of dioxygen. Suitable catalysts which are more selective for the oxidation of propylene to acrolein and acrolein to acrylic acid can be prepared from bismuth, cobalt, iron, nickel, tin salts, and molybdic, molybdic phosphoric, and molybdic silicic acids. Preferred second-stage catalysts generally are complex oxides containing molybdenum and vanadium. Other components, such as tungsten, copper, tellurium, and arsenic oxides, have been incorporated to increase low temperature activity and productivity.

Factors upon which catalyst performance depends include composition, the methods of preparation, support, and calcination conditions. Other key properties include, In addition to chemical performance requirements, other key properties include surface area, porosity, density, pore size distribution, hardness, strength, and resistance to mechanical attrition.

Patents claiming specific catalysts and processes for their use in each of the two reactions include: U.S. Pat. No. 3,962,322 and U.S. Pat. No. 3,939,096 both in the name of Peter C. Richardson; U.S. Pat. No. 4,092,354 in the name of Tatsuo Shiraishi, Susumu Kishiwada and Yoshihiko Nagaoka; U.S. Pat. No. 4,203,906 in the name of Masahiro Takada, Hiroyuki Uhara, and Takahisa Sato; U.S. Pat. No. 4,537,874 in the name of Takahisa Sato, Masahiro Takada, Michio Ueshima, and Isao Nagai; and U.S. Pat. No. 4,537,874 in the name of Masahiro Takada, Ryuji Aoki and Takahisa Sato, which patents are incorporated herein by reference.

A preferred class of catalysts useful, according to the present invention, are based on bismuth molybdate for the first stage and molybdenum vanadium oxides for the second stage. Improvements in minor component composition and catalyst preparation have resulted in yields that can reach the up to about 85 and even over 90 percent and lifetimes of several years under optimum conditions. However, commercial facilities are generally operated under more productive conditions than those optimum for yield and life, because the economically most attractive yields and productive lifetimes may be somewhat lower.

Feeds for the oxidation contain a mixture of propylene, air, steam, and nitrogen. Steam and nitrogen are needed to help control reactor hot-spot temperatures, and to provide a mixture which is not flammable. Beneficially, feed compositions range up to about 9 percent propylene on molar basis. Gaseous mixtures in the oxidation reactors are kept too low in oxygen to be flammable during normal operation. Reactor start-up and shutdown procedures are likewise designed to avoid flammable feed mixtures.

In commercial facilities the catalytic oxidation section typically consists of two tubular, fixed-bed reactors which are operated in series. Preferably the oxidation reactors are of the fixed-bed shell-and-tube type from about 3 to 5 meters long and about 1.9 to about 3.0 centimeters in diameter. Each reactor comprises between about 15,000 and about 35,000 tubes. The tubes are packed with catalyst, and optionally a small amount of inert material at the top serving as a preheater section for the feed gases. The reactor tubes are cooled on the shell side by circulated a coolant which is typically a molten salt. Temperature of the coolant is controlled by heat exchangers which may generate steam.

Vaporized propylene is mixed with steam and air and fed to the first-stage reactor wherein propylene is predominately converted to acrolein. The feed composition is typically from about 5 to about 7 percent of propylene, up to about 35 percent of steam, and the balance a gaseous source of dioxygen, typically compressed air or a mixture of compressed air and absorber vent gas. The heat of reaction is removed by a molten salt bath which is circulated through a steam generator to control the temperature of the molten salt to temperatures from about 300° to about 400° C. by generating steam at elevated pressure.

The preheated gases react exothermically over the first-stage catalyst with the peak temperatures depending on conditions and catalyst selectivity. The conversion of propylene to oxides of carbon, i.e. carbon dioxide and carbon monoxide, is more exothermic than its conversion to acrolein. At the end of the catalyst bed the temperature of the mixture drops toward that of the molten salt coolant. Because acrolein at such elevated temperatures can undergo exothermic homogeneous decomposition to carbon oxides, i.e. carbon monoxide and carbon dioxide, first-stage reactor effluent is typically cooled to about 200° to about 250° C. in an interstage cooler to prevent homogeneous and non-selective oxidation of acrolein taking place in the pipes leading to the second-stage reactor.

Compressed air is preferably admixed with the first-stage reactor effluent upstream of second-stage oxidation reactor to provide oxygen for the oxidation reaction. The acrolein-rich gaseous mixture containing some acrylic acid is then passed to the second-stage reactor, which is similar to the first-stage reactor, but packed with a catalyst designed for selective conversion of acrolein to acrylic acid. The temperature of the effluent from the second-stage reactor again approximates that of the salt coolant. The heat of reaction is recovered as steam in external waste-heat boilers, and may be further cooled to about 220° C. and/or directly quenched.

Advantageously, the oxidations are operated at the lowest temperature consistent with high conversion. Conversion increases with temperature; the selectivity generally decreases only with large increases in temperature. Catalyst life also decreases with increasing temperatures. Catalysts are designed to give high performance over a range of operating conditions permitting gradual increase of salt temperature over the operating life of the catalysts to maintain productivity and selectivity near the initial levels, thus compensating for gradual loss of catalyst activity.

The gaseous effluent from the second-stage oxidation reactor is transferred into the aqueous quench system wherein effluent is cooled from about 250° C. to about 80° C. or less by contact with aqueous acrylic acid. The gas passes through the absorber to complete the recovery of product. Water is fed to the quench system at about 30° to about 60° C. to minimize acrylic acid losses and the vent gas is sent to a flare or to a furnace to convert all residual organic material to waste gas. Some of the vent gas may be recycled to the first-stage reactor feed to allow achievement of optimum oxygen-to-propylene ratio at reduced steam levels. If the resulting oxygen level is too low for best performance in the second-stage oxidation, an interstage feed of supplemental air, or air and steam, may be introduced. The aqueous effluent from the quench system is particularly suitable aqueous solution comprising acid values for use in recovery and refining acid values according to the invention.

The acid values of acrylic acid and acetic acid are extracted from the aqueous absorber effluent with an immiscible solvent predominately comprising propyl acetate and a cyclohexane. Advantageously, the extraction is performed using from about 5 to about 10 theoretical stages in a continuous tower with counter current flow of aqueous and immiscible solvent phases.

Acrylic acid is separated from the extraction solvents by distillation. Acrylic acid is a heat sensitive product which can dimerize and polymerize. Dimerization results in loss of product, and polymerization can cause fouling of equipment. Recovery and refining acid values according to the invention beneficially reduce and/or prevent many of these undesirable reactions through the use of mild conditions, such as vacuum distillations, and injection of polymerization inhibitors.

The extract is vacuum-distilled in the solvent recovery column, which is operated at low bottom temperatures to minimize the formation of polymer and dimer and is designed to provide acrylic acid-free overheads for recycle as the extraction solvent. A small aqueous phase in the overheads is mixed with the raffinate from the extraction step. This aqueous material is stripped before disposal both to recover extraction solvent values and minimize waste organic disposal loads.

Beneficially, mild conditions and short residence times to minimize dimer formation are maintained throughout the separations section. In addition, free-radical polymerization inhibitors are fed to each unit to prevent polymer formation and resulting equipment failure.

BRIEF DESCRIPTION OF PREFERRED EMBODIMENTS OF THE INVENTION

While this invention is susceptible of embodiment in many different forms, this specification and accompanying drawing disclose only some specific forms as an example of the use of the invention. In particular, preferred embodiments of the invention which include quenching the gaseous mixture with an aqueous quench liquid to obtain an aqueous solution comprising the acid values; contacting the aqueous solution with an immiscible extraction solvent; and an integrated sequence of distillations and phase separations to recover for recycle organic components of the extraction solvent, and obtain valuable acrylic acid and acetic acid products are illustrated and/or described.

The invention is not intended to be limited to the embodiments so described, and the scope of the invention will be pointed out in the appended claims.

Apparatus of this invention is used with certain conventional components the details of which, although not fully illustrated or described, will be apparent to those having skill in the art and an understanding of the necessary function of such components. Examples of plant ancillaries not illustrated or described include; facilities for preparation and distribution of polymerization inhibitor solutions, steam ejector or vacuum pump systems to maintain the required operating pressures for distillations at mild conditions of temperature, collection and disposal systems for waste liquids, and emergency vent systems.

More specifically with reference to the FIGURE, which is a schematic illustration of an integrated solvent extraction and distillation process according to a preferred embodiment of the invention, where counter-current liquid—liquid separation of acids from aqueous solution is illustrated as extraction column 30; recovery of the extraction solvents is illustrated as solvent separation column 40, raffinate stripping tower 70 and decantation drum 80; and distillation means for obtaining valuable acrylic acid and acetic acid products is illustrated as acrylic acid separation tower 50 and acetic acid separation tower 60.

During operation of the integrated processes for recovery and refining acid values from a gaseous mixture obtainable by gas-phase catalytic oxidation of propylene, an aqueous solution which contains the acid values is obtained by quenching the gaseous products of oxidation with an aqueous quench liquid.

The gaseous mixture enters the top of the quench column and is quenched with a spray of recirculated and cooled liquid which is mainly water, acrylic acid, and acetic acid. The quench column advantageously operates at temperatures in a range from about 0° to about 100° C., preferably at temperatures in a range from about 5° to about 95° C., and more preferably at temperatures in a range from about 25° to about 75° C.

The aqueous solution is fed from the quench tower or intermediate storage (not shown) through conduit 22 and into the upper part of extraction column 30. A stream of organic extraction solvents is fed from solvent storage tanks (not shown) or directly through extraction solvents manifold 28 and dispersed into the lower part of extraction column 30.

In this embodiment the extraction solvent system comprises isopropyl acetate and from about 45 to about 65 percent cyclohexane based upon total weight of isopropyl acetate and cyclohexane for best results. The extraction column is, for example, a perforated plate, or sieve plate column. The more-dense, continuous aqueous phase flows downward through the column while the less-dense, dispersed organic phase flows upward. After disengagement from the aqueous phase in the top of extraction column 30, extract flows through conduit 32, heat exchanger 34, conduit 36, and into solvent separation tower 40. Raffinate from the bottom of extraction column 30 is transferred through conduit 38 into stripper feed manifold 86, stripper feed/bottoms exchanger 74, and therefrom into the raffinate stripping tower 70 through conduit 76.

An overhead stream of vapors rich in the low-boiling component of the solvent system, cyclohexane, flows from solvent separation tower 40 through conduit 46 and into solvent condenser 48. Liquids from condenser 48 are transferred through conduit 82 and into solvents decantation drum 80. The less-dense organic phase is transferred from decantation drum 80 through conduit 24. A portion of the organic phase is transferred into solvent separation tower 40 as reflux through conduit 26. Another portion of the organic phase is transferred through conduit 88 into solvent storage tanks (not shown) or directly through extraction solvents manifold 28 and into extraction column 30.

A more-dense aqueous phase is transferred from decantation drum 80 through conduit 84 into raffinate feed manifold 86, the raffinate stripper feed/bottoms exchanger 74 and therefrom into raffinate stripping tower 70 through conduit 76. The raffinate stripping tower 70 is used to recover solvents from aqueous waste streams. The predominate aqueous waste streams are raffinate from extraction column 30, the water phase from the solvents decantation drum 80, and condensate from a recovery vacuum ejector system (not shown). These combined feeds are preheated in the raffinate stripper feed/bottoms exchanger 74. Live steam is supplied to raffinate stripping tower 70 through conduit 75 from a source of low pressure steam (not shown). The overhead vapor stream from the raffinate stripping tower is recycled to the into solvent condenser 48 through conduit 78. A liquid wastewater stream is withdrawn from the bottom of stripping tower 70 through conduit 72. After the wastewater stream is cooled in the raffinate stripper feed/bottoms exchanger 74, the wastewater is routed to the bio-treatment plant (not shown).

As needed in order to maintain suitable conditions of separation in tower 40, liquid from the bottom thereof circulates through conduit 43, reboiler 44 and into the tower through conduit 45. A liquid stream containing the acid values as the predominant components and the high-boiling component of the solvent system, isopropyl acetate, flows from the bottom solvent separation tower 40 through conduit 42 and into acrylic acid separation tower 50 as tower feed. Beneficially, levels of the low-boiling component of the solvent system, cyclohexane, in the liquid feed to acrylic acid separation tower 50 are less than 10 percent, preferably in a range from about 1 to about 5 percent cyclohexane based upon total weight of isopropyl acetate and cyclohexane present in the feed.

A liquid stream containing predominantly acrylic acid flows from the bottom acrylic acid separation tower 50 through conduit 52 and into intermediate storage or an acrylic acid purification unit (not shown). As needed in order to maintain suitable conditions of separation in tower 50, liquid from the bottom thereof circulates through conduit 53, reboiler 54 and into the tower through conduit 55. Beneficially, total level of water and the components of the extraction solvent system, isopropyl acetate and cyclohexane, in the acrylic acid stream from the bottom acrylic acid separation tower 50 is less than about 1 percent, preferably less than about 0.5 percent based upon total weight of the stream.

Typically the recovered acrylic acid is further refined in an acrylic acid purification unit (not shown) to produce one or more grades of acrylic acid products suitable for particular end use, e.g. an ester grade acrylic acid used to produce acrylate esters. Glacial acrylic acid grade is sold as a commercial commodity. Different grades of acrylic acid product may require different polymerization inhibitors and differ in the amount of and type of trace impurities present.

An overhead vapor stream rich in the high-boiling component of the solvent system, isopropyl acetate and containing acetic acid flows from acrylic acid separation tower 50 through conduit 55 and into condenser 56. Condensate is transferred through conduit 58 and into acetic acid separation tower 60. A portion of the condensate is returned to the tower as reflux through conduit 57.

A liquid stream containing predominantly acetic acid flows from the bottom acetic acid separation tower 60 through conduit 62 and into acetic acid rundown tanks (not shown). As needed in order to maintain suitable conditions of separation in tower 60, liquid from the bottom thereof circulates through conduit 63, reboiler 64 and into the tower through conduit 65.

An overhead vapor stream rich in the high-boiling component of the solvent system, isopropyl acetate and essentially free of acid values flows from acetic acid separation tower 60 through conduit 65 and into condenser 66. Condensate is transferred through conduit 68 and into solvent storage tanks (not shown) or directly through extraction solvents manifold 28 and into extraction column 30. A portion of the condensate is returned to the tower as reflux through conduit 67.

Preferred embodiments of the invention recover an acrylic acid product which contains at least 90 percent of the acrylic acid contained in the aqueous solution.

EXAMPLES OF THE INVENTION

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

Equipment

A stainless steel Otto-York reciprocating plate extraction unit was installed in a 12 foot section of a glass column with a 1 inch internal diameter. At either end of the 1 inch diameter section, the internal diameter of column expanded to a diameter of 2 inches. Feed and solvent were stored in 10 gallon stainless steel tanks equipped with piston pumps capable of pumping up to 500 mL/min. Both pumps were calibrated with water. The pump head in the feed pump was stainless steel, and the pump head in the solvent pump was ceramic. Raffinate and extract were collected in similar tanks. Sample ports were located in the raffinate and extract return lines. All tubing was ⅜" diameter 304 type stainless steel.

The Otto-York extraction column was run with counter current flow of feed and solvent. Because the feed solution had a higher density than the solvent solutions, the feed was introduced into the column at a point just below the top expansion section. The lower density solvent was introduced into the column at a point just above the lower expansion section. Where the solvent had the higher flow rate than the feed, solvent was used as the continuous phase, and the feed was the dispersed phase. In this configuration the extract exited the column above the top expansion section and the raffinate, exited below the bottom expansion section. An interface was maintained in the bottom expansion section, and product flow rates were controlled, by adjustment of the raffinate control valve.

General Procedure

For each startup, the column was first completely filled with solvent, the continuous phase. The reciprocator was set at about 150 RPM, and the solvent pump turned off. The feed pump was then turned on. When the feed bubbles reached the solvent entry point near the bottom of the column, the solvent pump was turned back on, and the pump rates were adjusted to the desired set-points. The raffinate control valve was adjusted to maintain an interface in the bottom expanded section of the column. Literature results show that column flooding occurs as the rate of reciprocation is increased and that the most efficient operation is at a point just below flooding. Therefore, the rate of reciprocation was increased until the column flooded, and then decreased to the point just below flooding. The column was allowed to line-out for about 5 column turnovers after startup, and about 3 column turnovers for subsequent changes of operating conditions.

Feed and solvent samples were drained from sample valves at the bottoms of the holding tanks. Raffinate and extract were taken from the sample ports in the raffinate and extract return lines after the column had lined-out. All samples were analyzed by gas chromatography for composition. Feed, raffinate, and extract samples were titrated for acids, and extract samples were also submitted for water content by Karl Fisher titration.

Example 1

This example demonstrates the liquid—liquid extraction of aqueous acrylic acid feed using 40 percent isopropyl acetate in cyclohexane as solvent according to the invention. A summary of the results is presented in Table I. The acrylic acid extracted was from about 99.45 to 99.94 percent. At the solvent to feed ratio of 2.00 stage height was 341 cm, and at solvent to feed ratio of 1.93 stage height was reduced even more to 299 cm.

Example 2

This example demonstrates the liquid—liquid extraction of aqueous acrylic acid feed using 60 percent isopropyl acetate in cyclohexane as solvent according to the invention. A summary of the results is presented in Table II. The acrylic acid extracted was from about 99.82 to 99.62 percent.

Comparative Example

This comparative example is to illustrate the essential role of cyclohexane in the solvent system as compared to the solvent system using benzene which is classified as a carcinogen. A summary of the results is presented in Table III for the liquid-liquid extraction of aqueous acrylic acid feed using 40 percent isopropyl acetate in benzene as solvent. The acrylic acid extracted was from about 99.79 to 99.92 percent. With this solvent system stage heights were 448 cm and higher at 460 cm.

TABLE I

Liquid—Liquid Extraction of Aqueous Acrylic Acid Feed Using 40% Isopropyl Acetate in Cyclohexane as Solvent

| Ratio, Solvent to Feed | Total Flow, L/hr | Water Loss, % | Stage Height, cm | Volumetric Efficiency, m²/hr |
|---|---|---|---|---|
| 2.00 | 28.96 | 24.25 | 341 | 84.83 |
| 2.32 | 21.01 | 26.30 | 488 | 43.05 |
| 2.27 | 11.79 | 24.18 | 698 | 16.89 |
| 1.93 | 25.10 | 26.55 | 299 | 84.03 |

Where Volumetric Efficiency is ratio of Total Flow to Stage Height.

TABLE II

Liquid—Liquid Extraction of Aqueous Acrylic Acid Feed Using as Solvent 60% Isopropyl Acetate in Cyclohexane

| Ratio, Solvent to Feed | Total Flow, L/hr | Water Loss, % | Stage Height, cm | Volumetric Efficiency, m²/hr |
|---|---|---|---|---|
| 1.91 | 24.28 | 20.66 | 661 | 36.71 |
| 2.53 | 18.84 | 16.02 | 948 | 19.88 |
| 1.98 | 18.97 | 16.72 | 817 | 23.22 |
| 1.49 | 18.82 | 18.56 | 744 | 25.31 |

Where Volumetric Efficiency is ratio of Total Flow to Stage Height.

TABLE III

Liquid—Liquid Extraction of Aqueous Acrylic Acid Feed Using as Solvent 40% Isopropyl Acetate in Benzene

| Ratio, Solvent to Feed | Total Flow, L/hr | Water Loss, % | Stage Height, cm | Volumetric Efficiency, m²/hr |
|---|---|---|---|---|
| 1.42 | 26.10 | 12.48 | 460 | 56.71 |
| 1.50 | 26.09 | 22.93 | 448 | 58.23 |

Where Volumetric Efficiency is ratio of Total Flow to Stage Height.

For the purposes of the present invention, "predominantly" is defined as more than about fifty percent. "Substantially" is defined as occurring with sufficient frequency or being present in such proportions as to measurably affect macroscopic properties of an associated compound or system. Where the frequency or proportion for such impact is not clear substantially is to be regarded as about twenty percent or more. The term "Essentially" is defined as absolutely except that small variations which have no more than a negligible effect on macroscopic qualities and final outcome are permitted, typically up to about one percent.

Examples have been presented and hypotheses advanced herein in order to better communicate certain facets of the invention. The scope of the invention is determined solely by the scope of the appended claims.

That which is claimed is:

1. A process for recovery of acid values from a gaseous mixture formed by catalytic oxidation of propylene with a gaseous source of dioxygen which process comprises:
    quenching the gaseous mixture comprising acid values of acrylic acid and acetic acid, steam and one or more non-condensable gas with an aqueous quench liquid to form an aqueous solution comprising acid values;
    contacting the aqueous solution with an immiscible solvent comprising propyl acetate and a cyclohexane to form an organic extract comprising acid values and a major portion of the propyl acetate, and an aqueous raffinate comprising a minor portion of the propyl acetate;
    fractionating the organic extract as by distillation to obtain a high boiling fraction substantially free of cyclohexane and a low boiling fraction comprising cyclohexane and steam; and
    thereafter fractionating the high boiling fraction to obtain an acrylic acid product substantially free of propyl acetate and a propyl acetate fraction comprising propyl acetate and acetic acid.

2. The process according to claim 1 wherein the immiscible solvent comprises isopropyl acetate and no less than about 25 percent of cyclohexane based upon the total weight of isopropyl acetate and cyclohexane.

3. The process according to claim 1 wherein the immiscible solvent comprises isopropyl acetate and from about 30 to about 80 percent of cyclohexane based upon the total weight of isopropyl acetate and cyclohexane.

4. The process according to claim 1 wherein the contacting is carried out using a continuous extraction system with counter-current flow of the aqueous solution and the immiscible solvent.

5. The process according to claim 1 wherein the aqueous solution comprises from about 30 to about 70 percent of acrylic acid, from about 0.5 to about 7.5 percent of acetic acid and from about 15 to about 65 percent of water based upon the weight of the aqueous solution.

6. The process according to claim 1 wherein the high boiling fraction contains less than 10 percent by weight of cyclohexane.

7. The process according to claim 1 which further comprises condensing at least a portion of the low boiling fraction thereby forming condensate comprising immiscible aqueous and cyclohexane phases, and separating a recovered cyclohexane phase from the aqueous phase.

8. The process according to claim 1 wherein the acrylic acid product contains less than 0.1 percent by weight of acetic acid.

9. The process according to claim 1 wherein the propyl acetate fraction comprises from about 80 to about 93 percent of propyl acetate and from about 2 to about 15 percent of acetic acid based upon the weight of the propyl acetate fraction.

10. The process according to claim 1 wherein at least 90 percent of the acrylic acid contained in the aqueous solution is recovered in the acrylic acid product.

11. A process for recovery of acid values from a gaseous mixture formed by catalytic oxidation of propylene with a gaseous source of dioxygen which process comprises:

quenching the gaseous mixture comprising acid values of acrylic acid and acetic acid, steam and one or more non-condensable gas with an aqueous quench liquid to form an aqueous solution comprising acid values;

contacting the aqueous solution with an immiscible solvent comprising propyl acetate and a cyclohexane to form an organic extract comprising acid values and a major portion of the propyl acetate, and an aqueous raffinate comprising a minor portion of the propyl acetate;

fractionating the organic extract as by distillation to obtain a high boiling fraction substantially free of cyclohexane and a low boiling fraction comprising cyclohexane and steam;

fractionating the high boiling fraction to obtain an acrylic acid product substantially free of propyl acetate and a propyl acetate fraction comprising propyl acetate and acetic acid; and fractionating the propyl acetate fraction to obtain an acetic acid product substantially free of propyl acetate and a recovered propyl acetate fraction.

12. The process according to claim 11 wherein the immiscible solvent contains at least a portion of the recovered propyl acetate fraction.

13. The process according to claim 11 which further comprises condensing at least a portion of the low boiling fraction thereby forming condensate comprising immiscible aqueous and cyclohexane phases, and separating a recovered cyclohexane phase from the aqueous phase, and wherein the immiscible solvent contains at least a portion of the recovered cyclohexane.

14. The process according to claim 13 which further comprises forming a stripping tower feed by combining at least a portion of the separated aqueous phase with at least a portion of the aqueous raffinate, and contacting the stripping tower feed with steam to recover solvents and obtain wastewater suitable for bio-treatment.

15. A process for recovery of acid values from a gaseous mixture formed by catalytic oxidation of propylene with a gaseous source of dioxygen which process comprises:

quenching the gaseous mixture comprising acid values of acrylic acid and acetic acid, steam and one or more non-condensable gas with an aqueous quench liquid to form an aqueous solution comprising acid values;

contacting at least a portion of the aqueous solution with an immiscible solvent comprising propyl acetate and a cyclohexane to form an organic extract comprising acid values and a major portion of the propyl acetate, and an aqueous raffinate comprising a minor portion of the propyl acetate;

fractionating at least a portion of the organic extract as by distillation to obtain a high boiling fraction substantially free of cyclohexane and a low boiling fraction comprising cyclohexane and steam;

condensing at least a portion of the low boiling fraction to form a mixture of at least two immiscible liquid phases, and separating from the mixture a recovered cyclohexane phase containing less than about 2 percent by weight of water;

fractionating the high boiling fraction to obtain an acrylic acid product substantially free of propyl acetate and a propyl acetate fraction comprising propyl acetate and acetic acid; and fractionating the propyl acetate fraction to obtain an acetic acid product substantially free of propyl acetate and a recovered propyl acetate fraction.

16. The process according to claim 15 wherein the immiscible solvent contains at least a portion of the recovered cyclohexane phase.

17. The process according to claim 15 wherein the immiscible solvent contains at least a portion of the recovered propyl acetate fraction and at least a portion of the recovered cyclohexane phase.

18. The process according to claim 15 wherein the fractionating of the organic extract is carried out in a continuous distillation system using as reflux at least a portion of the recovered cyclohexane.

19. The process according to claim 15 wherein the immiscible solvent, comprising propyl acetate and a cyclohexane, contains less than a total of about 2 percent by weight of acrylic acid and acetic acid.

20. The process according to claim 15 wherein more than 90 percent of the acrylic acid contained in the aqueous solution is recovered in the acrylic acid product.

* * * * *

UNITED STATES PATENT AND TRADEMARK OFFICE
CERTIFICATE OF CORRECTION

PATENT NO. : 6,737,546 B2
DATED : May 18, 2004
INVENTOR(S) : Wagner et al.

It is certified that error appears in the above-identified patent and that said Letters Patent is hereby corrected as shown below:

Column 7,
Line 33, "Other key properties include, In addition to chemical performance requirements, other key properties include surface" should read -- In addition to chemical performance requirements, other key properties include surface --
Lines 54-55, "can reach the up to" should read -- can reach up to --

Signed and Sealed this

First Day of March, 2005

JON W. DUDAS
*Director of the United States Patent and Trademark Office*